United States Patent [19]

Reich

[11] Patent Number: 5,068,617

[45] Date of Patent: Nov. 26, 1991

[54] CAPACITY PROBE FOR LIQUID MEASUREMENTS

[76] Inventor: Stefan J. Reich, Ulrichstr. 68, D-8021 Icking, Fed. Rep. of Germany

[21] Appl. No.: 373,922

[22] Filed: Jun. 30, 1989

[30] Foreign Application Priority Data

Jul. 1, 1988 [DE] Fed. Rep. of Germany ....... 3822344

[51] Int. Cl.$^5$ ............................................. G01R 27/26
[52] U.S. Cl. ..................................... 324/663; 324/687
[58] Field of Search ............... 324/663, 664, 666, 667, 324/668, 674, 675, 687, 689, 690, 464

[56] References Cited

U.S. PATENT DOCUMENTS

| | | | |
|---|---|---|---|
| 2,774,938 | 12/1956 | Edinborgh | 324/689 |
| 3,391,547 | 7/1968 | Kingston | 324/664 |
| 3,437,924 | 4/1969 | Tocanne | 324/690 |
| 3,784,897 | 1/1974 | Norrie | 324/688 |
| 3,793,585 | 2/1974 | Wilska | 324/668 |
| 4,272,718 | 6/1981 | Kashiuchi et al. | 324/668 |

Primary Examiner—Kenneth A. Wieder
Assistant Examiner—Maura K. Regan
Attorney, Agent, or Firm—Norman E. Brunell

[57] ABSTRACT

Capacitive device to measure changes in liquids, such as changes in the mixing ratio of composite liquids, utilizing capacity measured by an electrode probe. An isolating body is located between the electrodes in the liquid and causes a deviation of the field lines to lower the field strength on the electrodes to avoid measurement disturbances from dirt and air bubbles or other contaminants. Furthermore, circuitry for measuring the capacity independently of any disturbing effects of variable ion concentration in the liquid. This is carried out by separately evaluating the phase of a high-frequency signal on a resonance circuit connected to the electrodes.

2 Claims, 1 Drawing Sheet

CAPACITY PROBE FOR LIQUID MEASUREMENTS

BACKGROUND OF THE INVENTION

1. Field of the Invention

The present invention relates to an apparatus for measuring features of liquids which influence their dielectric characteristics, particularly the composition of the liquid, i.e. the ratio of components.

This measurement is used for example for observation and automatic refilling of the alcohol content in alcohol-water-mixtures, which are used in printing equipment as the so called "fountain-solution".

2. Description of the Prior Art

Prior art devices use a gauge or float valve which reacts to the specific weight of the mixture in accordance with the alcohol content, and, according to its floating level, actuates a switch. One of its shortcomings is the sensitivity to dirt, air bubbles, and mechanical movement. Moreover, an instantaneous exact reading of the measured value is difficult to obtain.

There are different methods which utilize the change of the dielectric constant to evaluate the water content of a material. German OS 3507507 describes a capacitive probe for use with fountain solution, this however only measures the filling level and not the composition of the liquid.

OS-DE 3518186 describes a method for evaluating the water content in alcohol using an approach based on capacity; OS-DE 2002168 describes an electrode probe for evaluation of a water-oil mixing ratio. OS-DE 3433740 and 2436344 describe probes for measuring the water content in butter. All the above methods are based on the evaluation of capacitance which appears at the electrodes of a capacity probe. These conventional techniques are not, however, suitable for measuring the mixing ratio when the water content represents the major portion of the mixture, and additionally when the water's electric conductivity is increased by certain added salts or buffering chemicals typically used in fountain-solutions, because of the resultant errors. Furthermore, having a high percentage of water causes the mixture to have a high dielectric constant (water has about 80), and this dielectric value is reduced only in a small amount by the added alcohol, relative to the high initial value. The commonly used values of alcohol percentages in fountain solutions are 3 to 25%.

Another disadvantage of conventional approaches is that contamination such as oil or ink residue will stick to the electrodes' surface and make the measurement inaccurate due to their own dielectric constant. Oil has an extremely small dielectric constant of about 3 and thus functions like an isolator in series with the capacitive path. The same happens with gas-bubbles which appear from fresh water and tend to stick the electrodes.

SUMMARY OF THE INVENTION

The primary object of the invention is to avoid the above shortcomings and to provide method and apparatus which is suitable for any measurement, contains no moving parts and therefore is insensitive to contaminate and motion.

In a first aspect, the invention provides apparatus for measuring the dielectric of a liquid including means for creating an alternating electric field in a liquid for detecting the electric field and an isolator in contact with the liquid within the electric field for modifying the field strength detected at the electrodes.

The present invention includes at least one electrically isolating body in the electrode probe, which is in touch with the liquid and is, located in the electric field to cause a deviation, extention, or narrowing of the electric field lines. This will reduce the field strength at the electrodes' surface. Electronic circuitry is provided for making measurements from the probe to determine capacitance and/or conductivity.

The isolator, located between the electrodes, has the effect that the field lines, on their way through the liquid from electrode to electrode, become deviated, e.g. extended or narrowed. The effect of this is a lower field strength on the electrodes' surface. This results in a relatively smaller capacity although the surface of the electrodes can have any desired area. By this, the following is achieved:

The electric field develops mainly in the liquid itself and not in the proximity of the electrodes;

sticking dirt does not have an essential influence on the field, due to the lowered field strength at the electrodes;

simultaneously, this reduction of field strength reduces the capacity as well as the conductivity caused by water ions, so that their damping influence on the capacity measurement can easily be compensated with circuitry according to the present invention;

in spite of this reduction, the main portion of the electric field strength remains in the liquid and does not accumulate in the isolator, as would be the case if the isolator would simply be a barrier completely covering the electrode or across the path in between.

One way to achieve this intended field deviation is through narrowing the field lines by leading them through a hole of an isolator, as described in one embodiment.

Another possibility is to extend the field lines, as shown in the second embodiment.

Both manners diminish the capacitance between the electrodes and thus decrease the field strength at the electrodes, and simultaneously concentrate the main part of field in the liquid itself.

The diminution of capacitance is not primarily caused by a smaller capacity in series with the circuit, as a simple isolator would do, but rather by the change of the path of the field lines in the measuring liquid.

Another object of the present invention is to provide apparatus for measuring changes which influence the dielectric value of the liquid in a manner insensitive to ionic concentration which would otherwise affect conductivity.

In another aspect, the present invention provides a method of measuring the dielectric of a liquid by positioning a probe in contact with the liquid to create an alternating electric field therein, forming a resonance circuit with the probe, loosely coupling the resonance circuit to a high frequency oscillator and measuring the phase relationship between signals in the oscillator and resonance circuits.

In still another aspect, the invention provides a method of measuring the dielectric of a liquid by measuring the real and imaginary components of the impedance of a probe in contact with the liquid, maintaining the phase angle between the components at a predetermined value and determining the dielectric from one of the components.

Electronic circuitry of the present invention described below enables the evaluation of the capacity at the electrode probe, compensating for any conductivity errors, by measuring the phase relation of a tank or resonance circuit consisting of the electrode probe and an inductor.

A method is disclosed for connecting the electrodes with electronic circuitry for separately measuring the real or in-phase component, which relates to the conductivity, and/or the blind or imaginary component, which relates to the capacity, of the whole complex impedance. This permits total compensation of one parameter (conductivity) to another (capacity) in the measurement process, e.g. using the conductivity output to correct the capacity-reading by mixing it into the capacity output in an adjustable amount as may be appropriate in particular applications.

Furthermore, the measuring of conductivity, which is also dependent on the composition of the liquid can be used as an essential or supplementary source to evaluate typical composition of the liquid.

Temperature compensation may be appropriate because water changes its capacity with temperature.

The invention may be used as a sensor particularly in printing processes, and having an output to trigger automatical refilling of alcohol in the composite liquid up to an adjustable desired value, whenever evaporation has diminished the alcohol percentage.

Although particularly developed for the use in alcohol-water mixings, the present invention includes comprehensively any other purpose of use.

DETAILED DESCRIPTION OF THE PREFERRED EMBODIMENTS

Figure 1:
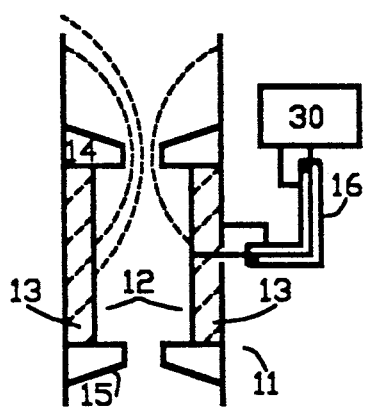
FIG. 1 shows a cross sectional view of one embodiment of the invention.

In particular, with regard now to FIG. 1, the outer metal tube 11 functions as one electrode. Concentrically inside of this, a smaller metal tube 12 is located as the second electrode. Collars 14 and 15 are made from isolating plastic material, each having a borehole. They hold the inner tube 12 and cover it, except for their two openings. The space between the tube walls is tightly filled with the isolating filling material 13. Both the electrodes are connected to the electronic circuitry 30 through the coaxcable 16. The field lines become narrowed in the holes of the collars 14 and 15, so that the main part of the field strength is located in this range.

Figure 2A:
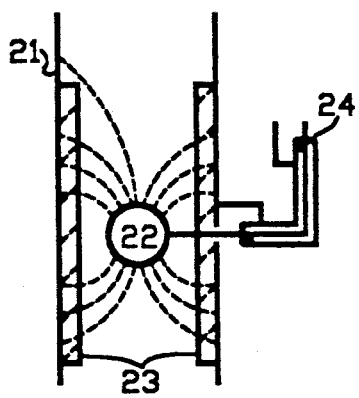
FIG. 2a shows a cross sectional view of another embodiment of the invention.

With regard now to FIG. 2a outer metal tube 21 serves as the larger electrode and is on its inside surface covered with the isolating tube 23, made of plastic, glass or similar isolating material.

Figure 2B:
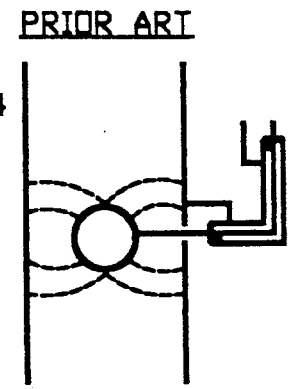
FIG. 2b shows the resultant field lines without the isolator of the invention.

The second electrode 22 is located in the inside space and is connected with the cable 26. The inside space is filled with the probe liquid. Because the area of the electrode 21 with its cover 23 is larger than the distance to the inner electrode 22, the field lines spread into an an essentially larger space than would be the case without the isolation 23, as shown in FIG. 2b.

The isolation 23 can favorably be a little shorter than the outer tube 21, so that the field lines can flow directly into the electrode 21 by the tube ends. Hereby, the field lines through avoiding the isolation are forced onto this longer path.

In general, it is possible to have the electrodes arranged in any other shape. Any material brought into the field of the probe liquid, if it has lower dielectric constant than the probe liquid itself, will cause the desired field decreasing and concentration effect, as soon as any deviation of the shape (not only the strength) of the field lines occurs.

Figure 3:
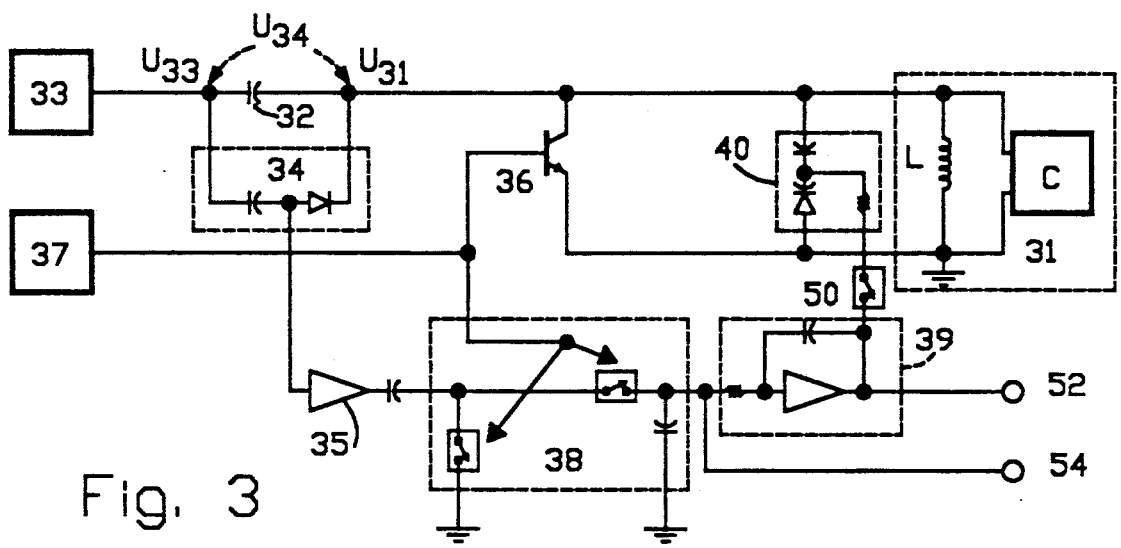
FIG. 3 shows a schematic of the circuitry for a preferred embodiment of the invention.
Figure 4:
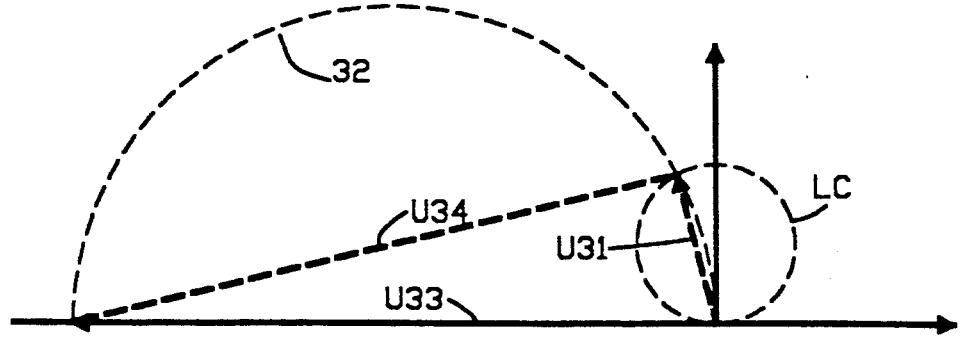
FIG. 4 shows a vector diagram of the relationship of important signals in the circuitry of FIG. 3.

With regard now to FIGS. 3 and 4, capacitive probe c together with the inductivity L make up a resonance circuit 31. This circuit is loosely coupled to the HF oscillator 33 through the capacitor 32. HF oscillator 33 may operate at 50 MHz. The voltage difference U34 between oscillator voltage U33 and the resonance circuit's instantaneous voltage U31 is measured in the rectifier 34 and amplified in the amplifier 35. If the resonance circuit and oscillator are tuned together, i.e. they resonate at the same frequency, the difference voltage U34 has essentially the same amplitude as the oscillator voltage U33, because U31 is orthogonal to U33, due to the capacitive coupling, and furthermore is essentially smaller in its amplitude than U33; as can be seen in FIG. 4.

At regular time intervals the transistor 36, driven from the low frequency clock oscillator (LFO) 37, is switched on and off. LFO 37 may conveniently produce a square ware at 80 Hz. This creates, in intervals, a complete damping of the resonance circuit 31 and so causes the amplitude of U31 to completely decay. In the case of resonance with 90 degrees phase difference, this damping has — as described above — no essential effect on the amplitude measured in rectifier 34. If, however, changes of the liquid composition create a detectable change of capacitance in the electrode, the resulting detunement creates a phase-shift and will be detected through rectifier 34 and amplifier 35, appearing as an amplitude ripple synchronous with the switching rythm.

This ripple will be converted into a DC-voltage by the switchmode or clocked rectifier 38, and brought to the input of the regulating amplifier 39. This amplifier drives and changes the bias voltage of the varicap circuitry 40 and thus shifts the resonance frequency of the resonance circuit 31 until resonance symmetry with 90 degrees phase is achieved again. The altered capacity of the varicap compensates for the initial change of the electrode capacity to complete the feedback loop.

The varicap voltage is a measure for this capacity change and is utilized to evaluate the mixing composition of the liquid.

In other words, if switch 50 is closed, output regulating amplifier 39 serves to adjust the voltage of varicap 40. This results in an error correcting feedback loop which maintains resonance. Output 52 is then proportional to the quantity to be measured, such as the alcohol concentration, in accordance with the physical operating parameters of varicap 40.

If switch 50 is open, the circuitry operates in an open loop fashion and output 54 represents the phase measurement related to the dielectric value of the composite liquid to be measured.

I claim:

1. A system for measuring the dielectric of a liquid comprising:
 a pair of capacitive electrodes for creating an alternating electric field in the liquid;
 means responsive to the electrodes for detecting the electric field; and
 isolating means in contact with the liquid for causing a narrowing or extension of the electric field between the electrodes, wherein the isolating means is positioned between the electrodes to cause a narrowing of the electric field by reducing the cross-sectional area of the electric field therebetween.

2. The system claimed in claim 1, wherein the pair of electrodes further comprises:
 an outer metal tube;
 a smaller inner metal tube positioned within the outer tube having a shorter axial dimension than the outer metal tube; and
 wherein the isolating means is positioned in the space between the tubes covering both ends of the inner tube except for at least one opening therethrough at each end of the inner tube.

* * * * *

UNITED STATES PATENT AND TRADEMARK OFFICE
CERTIFICATE OF CORRECTION

PATENT NO. : 5,068,617
DATED : Nov. 26, 1991
INVENTOR(S) : Stefan J. Reich It is certified that error appears in the above-identified patent and that said Letters Patent is hereby corrected as shown below:

COL. 1　LINE 67　After --in a liquid-- insert "to be measured, a pair of electrodes in contact with the liquid.";

COL. 2　LINE 5　After --and is-- delete ",";

Signed and Sealed this

First Day of June, 1993

Attest:

MICHAEL K. KIRK

Attesting Officer　Acting Commissioner of Patents and Trademarks